United States Patent [19]
Pinchuk et al.

[11] Patent Number: 5,236,659
[45] Date of Patent: Aug. 17, 1993

[54] TAILORING EXPANSION PROPERTIES OF BALLOONS FOR MEDICAL DEVICES

[75] Inventors: Leonard Pinchuk, Miami; Robert S. Shonk, Davie; Thomas Trotta, Miami, all of Fla.

[73] Assignee: Cordis Corporation, Miami Lakes, Fla.

[21] Appl. No.: 838,143

[22] Filed: Feb. 18, 1992

Related U.S. Application Data

[60] Division of Ser. No. 452,713, Dec. 19, 1989, Pat. No. 5,108,415, which is a division of Ser. No. 384,723, Jul. 24, 1989, Pat. No. 4,906,244, which is a continuation-in-part of Ser. No. 253,069, Oct. 4, 1988, abandoned.

[51] Int. Cl.$^5$ .................. B29C 49/08; B29C 49/64
[52] U.S. Cl. .................... 264/573; 264/532; 264/570; 264/235
[58] Field of Search ............... 264/573, 532, 523, 570, 264/235

[56] References Cited

U.S. PATENT DOCUMENTS

| R. 32,983 | 7/1989 | Levy ................... | 428/36.92 |
|---|---|---|---|
| 3,733,309 | 5/1973 | Wyeth et al. ........... | 260/75 T |
| 4,323,071 | 4/1982 | Simpson et al. ......... | 128/343 |
| 4,411,055 | 10/1983 | Simpson et al. ......... | 29/447 |
| 4,456,000 | 6/1984 | Schjeldahl et al. ...... | 604/49 X |
| 4,490,421 | 12/1984 | Levy ................... | 604/96 X |
| 4,820,349 | 4/1989 | Saab ................... | 128/344 |

FOREIGN PATENT DOCUMENTS

| 274411 | 7/1988 | European Pat. Off. . |
| 2011307 | 7/1979 | United Kingdom . |

OTHER PUBLICATIONS

Bard, Inc., "USCI The Innovation Continues . . . PE Plus II", 1985.

Primary Examiner—Catherine Timm
Attorney, Agent, or Firm—Lockwood, Alex, Fitzgibbon & Cummings

[57] ABSTRACT

Dilatation balloons are fabricated of a biaxially orientable material such as a nylon or a polyamide material, and they have an inflated, non-distended working profile as well as a stretched inflated profile which is achieved by applying pressure through a dilatation catheter or the like that is in excess of that needed to achieve the inflated, non-distended profile and which is adequate to effect dilatation or the like up to a maximum pre-bursting pressure application. The maximum pre-bursting size of the balloon can be tailored depending upon the needs of the particular balloon within a wide range of possible maximum pre-bursting sizes.

7 Claims, 6 Drawing Sheets

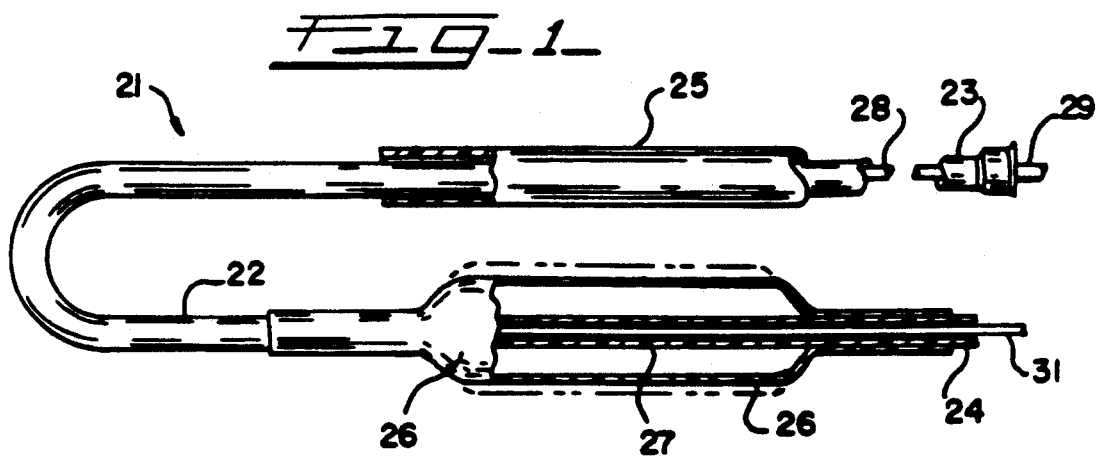
FIG_1_
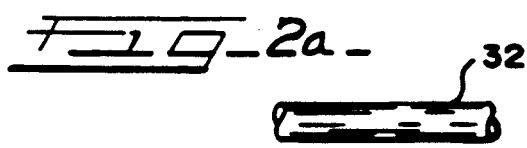
FIG_2a_
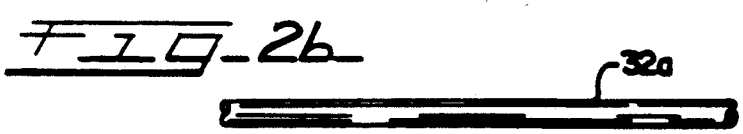
FIG_2b_
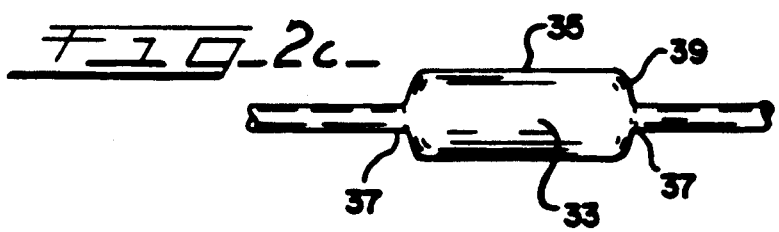
FIG_2c_
FIG_2d_
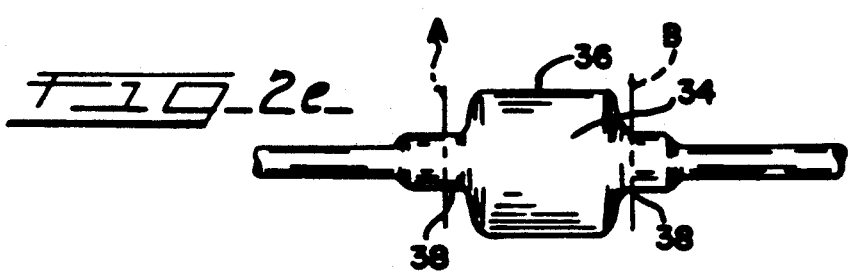
FIG_2e_

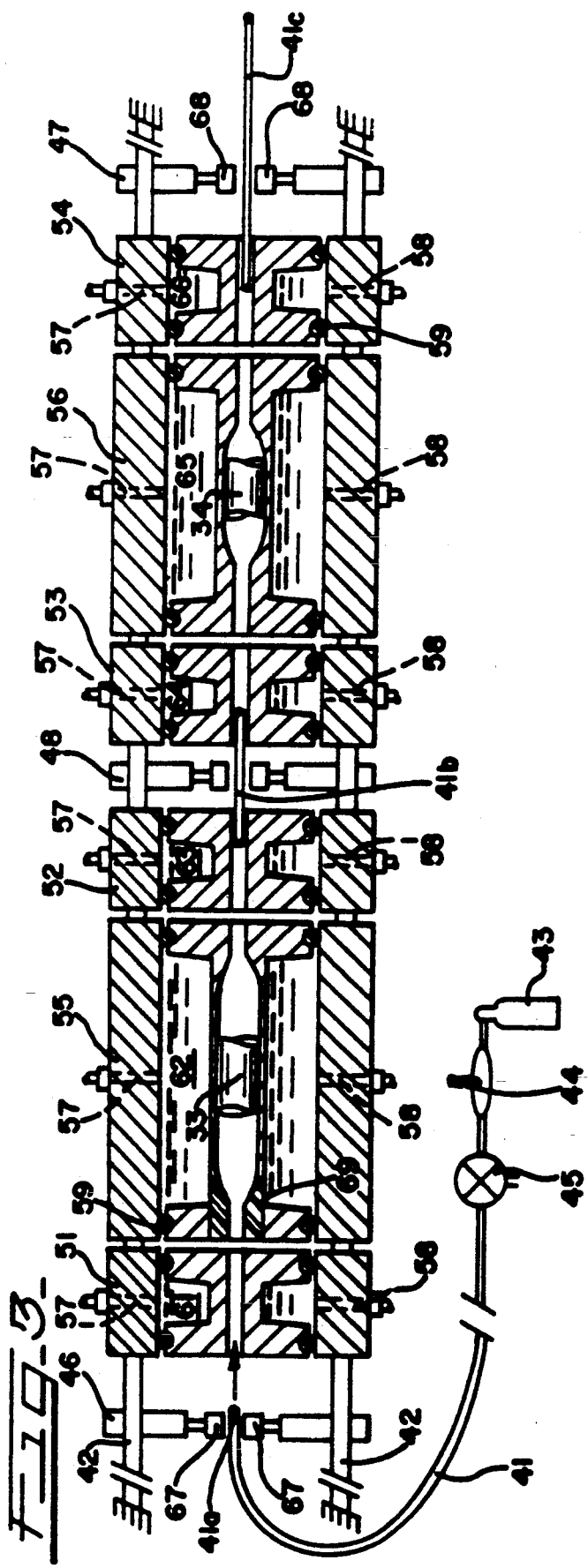

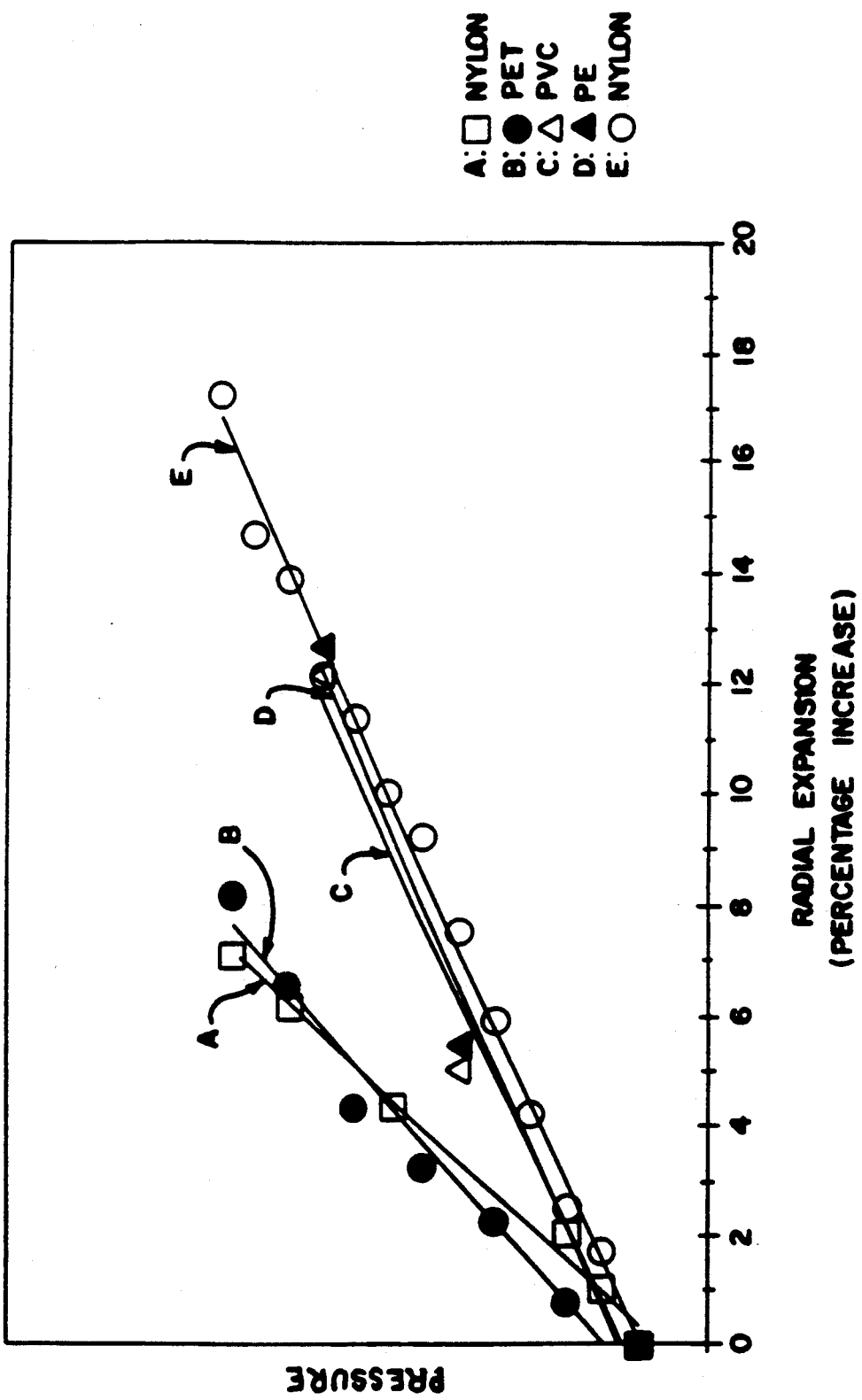

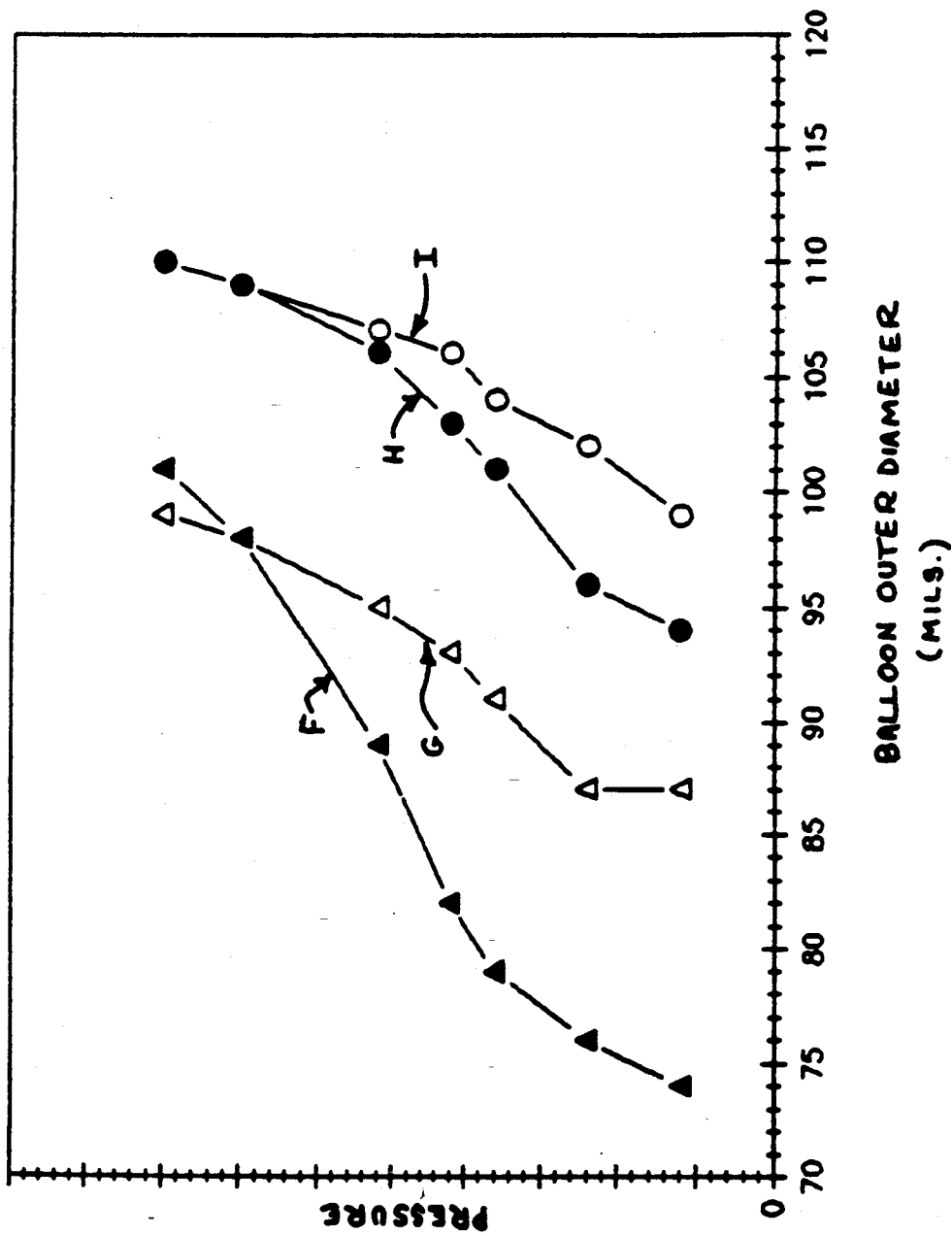

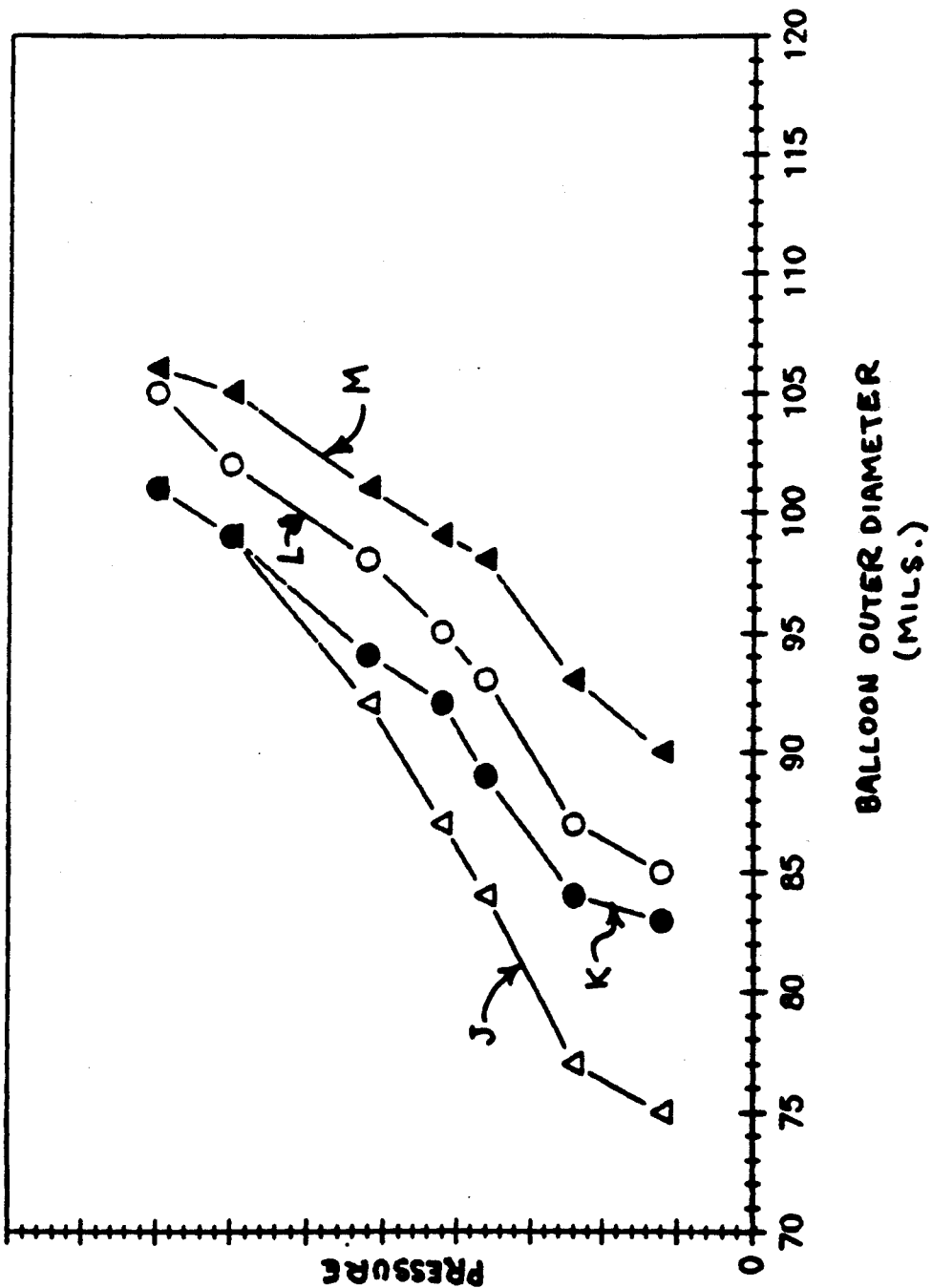
FIG-9-

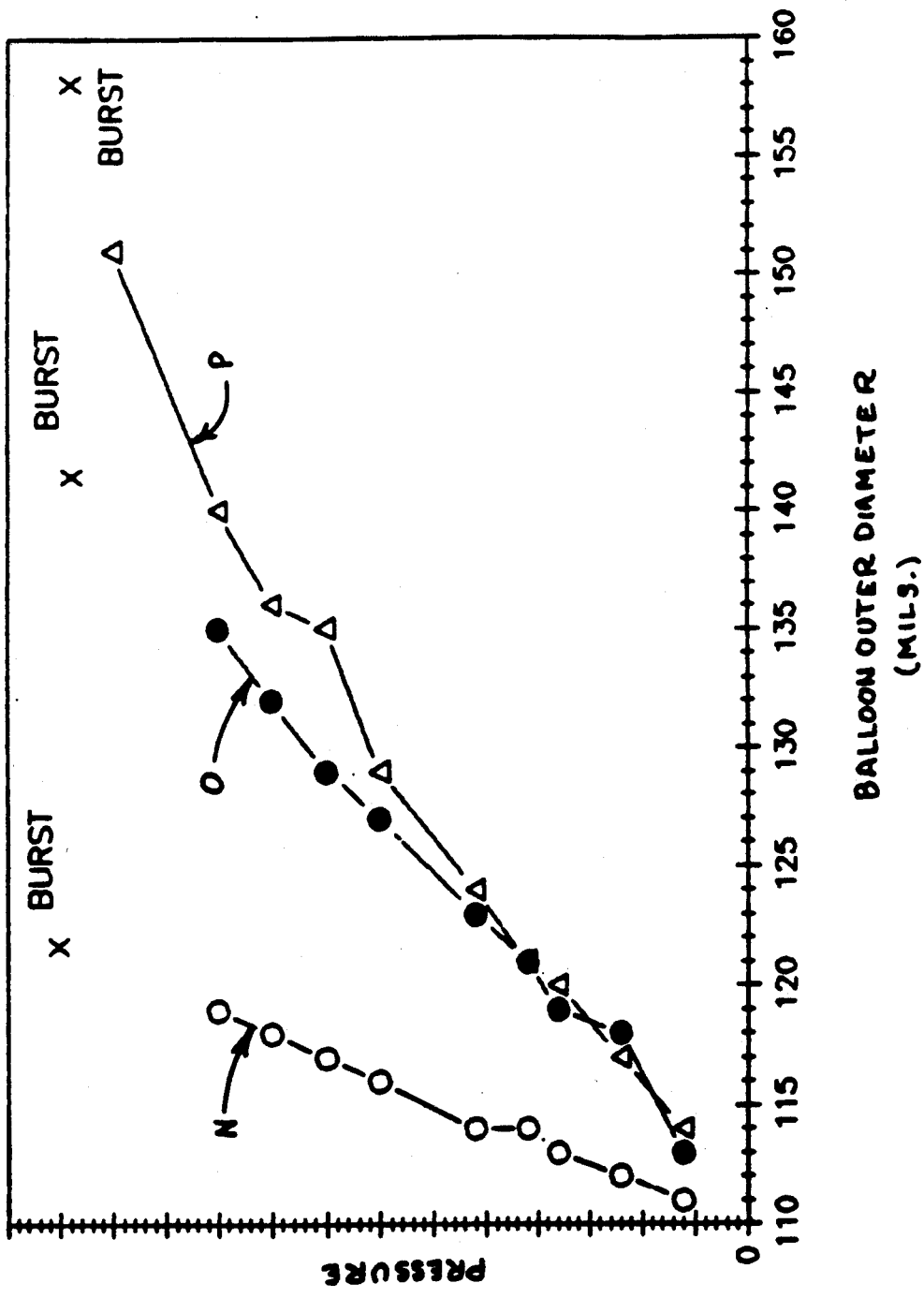

TAILORING EXPANSION PROPERTIES OF BALLOONS FOR MEDICAL DEVICES

This is a divisional of copending application Ser. No. 452,713, filed Dec. 19, 1989, now U.S. Pat. No. 5,108,415 which is a divisional of application Ser. No. 384,723, filed Jul. 24, 1989 (now U.S. Pat. No. 4,906,244), which is a continuation-in-part of application Ser. No. 253,069, filed Oct. 4, 1988. Now abandoned.

BACKGROUND AND DESCRIPTION OF THE INVENTION

The present invention generally relates to balloons for medical devices, as well as to processes and equipment for forming same. More particularly, the invention relates to medical or surgical balloons and to catheters incorporating them, such as those designed for angioplasty, valvuloplasty and urological uses and the like. The balloons exhibit the ability to be tailored to have expansion properties which are desired for a particular end use. The expansion property of particular interest is the amount or percentage of expansion or stretching beyond a non-distended inflated size at which the balloons are inflated to remove folding wrinkles but are not stretched. Balloons which are especially suitable in this regard are made of nylon or polyamide tubing that has been biaxially oriented into the desired balloon configuration.

Catheter balloons and medical devices incorporating them are well-known for use in surgical contexts such as angioplasty procedures and other medical procedures during which narrowings or obstructions in blood vessels and other body passageways are altered in order to increase blood flow through the obstructed area of the blood vessel. For example, in a typical balloon angioplasty procedure, a partially occluded blood vessel lumen is enlarged through the use of a balloon catheter that is passed percutaneously by way of the arterial system to the site of the vascular obstruction. The balloon is then inflated to dilate the vessel lumen at the site of the obstruction.

Essentially, a balloon catheter is a thin, flexible length of tubing having a small inflatable balloon at a desired location along its length, such as at or near its tip. Balloon catheters are designed to be inserted into a body passageway such as the lumen of a blood vessel, a heart passageway, a urological passageway and the like, typically with fluoroscopic guidance.

In the past, medical device balloon materials have included balloons having a wall thickness at which the material exhibits strength and flexibility that allow inflation to a working diameter or designated initial dilation diameter which, once achieved, is not surpassable to any significant degree without balloon breakage or substantially increasing the risk of balloon breakage. Balloons of these materials can be characterized as being substantially non-distensible balloons that are not stretchable, expandable or compliant to a substantial extent beyond this working diameter. Such substantially non-distensible balloons can be characterized as being somewhat in the nature of papers bags which, once inflated to generally remove folding wrinkles, do not further inflate to any significant degree. Polymeric materials of this substantially non-distensible type that are used or proposed for use as medical balloons include polyethylene terephthalates.

Other types of materials, such as polyvinyl chlorides and cross-linked polyethylenes can be characterized as being distensible in that they grow in volume or stretch with increasing pressure until they break. These materials are generally elastic and/or stretchable. When such extensible materials are used as medical balloons, the working diameter or designated dilation diameter of the balloon can be exceeded, based upon the stretchability of the material.

Substantially non-distensible balloons have at times been considered to be advantageous because they will not inflate significantly beyond their respective designated dilation diameters, thereby minimizing possible over-inflation errors. The theory is that one need only select a balloon such as an angiographic balloon that has an opened and inflated diameter which substantially corresponds to the dilation size desired at the obstruction site. However, physiological vessels such as arteries are generally tapered and do not always coincide with readily available catheter balloon dimensions, and at times it may be preferable to be able to increase the diameter of the balloon beyond what had been initially anticipated. With a substantially non-distensible balloon, such further extension is severely limited. On the other hand, certain non-distensible materials out of which medical balloons are made generally possess relatively high tensile strength values, which is typically a desirable attribute, especially for dilating tough lesions.

More readily distensible materials such as polyvinyl chloride typically exhibit a lower tensile strength and a larger elongation than a substantially non-distensible material such as polyethylene terephthalate. This relatively low tensile strength increases the risk of possible balloon failure. Due to their larger ultimate elongation, most readily distensible materials can provide a wide range of effective inflation or dilation diameters for each particular balloon size because the inflated working profile of the balloon, once achieved, can be further expanded in order to effect additional dilation. But this very property of having an expanded dilation range is not without its dangers because of the increased risk of overinflation that can damage the blood vessel being treated, and the overinflation risk may have to be compensated for by using balloon wall thicknesses greater than might otherwise be desired.

Although a material such as polyethylene terephthalate is advantageous from the point of view of its especially high tensile strength and its tightly controllable inflation characteristics, it has undesirable properties in addition to its general non-distensibility. In some situations, biaxial orientation of polyethylene terephthalate will impart excessive crystallinity to an angioplasty balloon, or the Young's modulus will be simply too high. Under these circumstances, the balloon itself or the thicker leg sections thereof will not readily fold over and down in order to provide the type of low profile that is desirable for insertion through a guiding catheter and/or through the cardiovascular system and especially through the narrowed artery which is to be dilated. The resistance to folding, or "winging," is an especially difficult problem when it comes to larger balloons, such as those intended for valvuloplasty applications.

Also, it has been observed that thin-walled materials such as polyethylene terephthalate have a tendency to form pin holes or exhibit other signs of weakening, especially when flexed. Such a tendency can require extreme care in handling so as to avoid inadvertent damage that could substantially weaken a polyethylene terephthalate medical balloon. Although it is known that a lower profile and more flexible balloon and balloon legs can be made by thinning the wall, thus thinned polyethylene terephthalate balloons become extremely fragile and may not survive insertion through the cardiovascular system with desired integrity and without pin-holing and/or rupture.

Materials such as polyethylene terephthalate do not readily accept coating with drugs or lubricants, which can be desirable in many applications. Polyethylene terephthalate materials are also difficult to fuse, whether by adherence by heating or with known biocompatible adhesives.

By the present invention, these undesirable and/or disadvantageous properties of substantially non-distensible medical balloons such as those made from polyethylene terephthalate materials are significantly eliminated. At the same time, many of the advantages of these types of materials are provided or approximated. Furthermore, the present invention realizes many of the advantages of the more elastomeric materials such as polyvinyl chloride, but without the disadvantages of relatively low tensile strength, and the possibility of excessive expandability that can lead to overinflation of a blood vessel or the like.

In summary, the present invention achieves these objectives and provides advantageous properties along these lines by forming and providing a catheter and medical catheter balloon constructed of a material that is of limited and generally controlled distensibility whereby expansion beyond the working or fully expanded but non-distended dilation profile of the balloon is possible, but only to a desired extent which can, within limits, be tailored to the particular needs of the balloon device. The invention includes utilizing a tailorable material such as a nylon material or a polyamide material that is formed into a biaxially oriented balloon by appropriate axial elongation, radial expansion and heat treatment procedures.

It is a general object of the present invention to provide an improved medical balloon and medical device incorporating a balloon.

Another object of the present invention is to provide an improved medical balloon that exhibits a controlled distensibility at high pressure.

Another object of the present invention is to provide an improved balloon and/or catheter and method of making same which provides a range of dilation capabilities while minimizing risks that could be associated with such flexibility.

Another object of the present invention is to provide an improved angioplasty catheter balloon molding method and apparatus that are especially suitable for forming tubing of tailorable materials such as nylon or polyamide into catheter balloons.

Another object of the present invention is to provide an improved means and method for biaxially orienting relatively amorphorous tubing into biaxially oriented medical balloons.

Another object of the present invention is to provide an improved balloon catheter that is readily coated with materials such as lubricating agents and the like which are advantageous for administration in association with balloon catheters.

Another object of this invention is to provide an improved balloon that exhibits a combination of good strength and desirable flexibility.

Another object of this invention is to provide a medical balloon that exhibits an ability to be readily fused to other components.

These and other objects, features and advantages of this invention will be clearly understood through a consideration of the following detailed description.

BRIEF DESCRIPTION OF THE DRAWINGS

In the course of this description, reference will be made to the attached drawings, wherein:

FIG. 1 is an elevational illustration, partially in cross-section, of a balloon catheter having a structure typical of that suitable for angioplasty;

FIGS. 2a, 2b, 2c, 2d and 2e are elevational illustrations of tubing as it is progressively processed to transform same into a medical balloon according to this invention;

FIG. 3 is a cross-sectional view illustrating a preferred apparatus for carrying out the processing steps illustrated in FIGS. 2a, 2b, 2c, 2d and 2e;

FIG. 4 is a plot of balloon size versus balloon inflation pressure for balloons made of a variety of materials, including nylon balloons tailored to provide different radial expansion properties;

FIGS. 5 and 6 are plots illustrating the function of heat setting on tailorability; and FIG. 7 is a plot illustrating the function of hoop expansion ratio on tailorability.

DESCRIPTION OF THE PARTICULAR EMBODIMENTS

An illustrative catheter is generally designated in FIG. 1 by reference numeral 21. Catheter 21 includes a catheter tube 22 having a proximal end 23 and a distal end 24. A guiding catheter 25 is also illustrated. A medical balloon 26 is shown secured to the distal portion of the catheter tube 22 in a location overlying one or more apertures 27 through the catheter tube. Extending through the lumen of the catheter tube 22 is an inner elongated body 28, such having a proximal end 29 and a distal tip end 31. The inner body 28 may be solid or have an internal lumen, depending upon the function that the inner body is to perform, whether it be simply a guiding function or whether it is intended to also provide the capability to insert materials into the bloodstream or measure parameters of the bloodstream, or the like.

Except for the balloon 26, all of these various components perform functions that are generally appreciated in the art. Typically with the aid of the guiding catheter 25, the inner body 28 and the catheter tube 22 are inserted into the cardiovascular system until the balloon is located at an occlusion site. At this stage, the balloon 26 is typically folded and collapsed, and it has an external diameter less than the inflated diameter illustrated in FIG. 1, to the extent that the balloon 26 is generally wrapped around the catheter tube 22. Once the balloon 26 is maneuvered to the location of the occlusion, a pressurized fluid is inserted at the proximal end 23 of the catheter tube 22 for passage through aperture 27 and for inflation of the balloon 26. This unfolds the balloon until it presents a relatively smooth outer surface or working profile for imparting forces that are radially outwardly directed at the desired site within the body in order to achieve the desired result of lesion dilation, occlusion reduction or similar treatment. In accordance with an important aspect of the invention, the passage of greater pressure against the inside surface of the balloon 26 permits the outer surface of the balloon 26 to transmit additional force to the lesion or the like, which may include actual further radially outwardly directed movement of the balloon 26 beyond its working profile, as illustrated in phantom in FIG. 1.

FIGS. 2a, 2b, 2c, 2d and 2e illustrate the transformation of a length of tubing 32 that is a material such as extruded nylon or polyamide into a biaxially oriented balloon 33 or a modified biaxially oriented balloon 34. Either balloon 33 or 34 possesses the ability to be first inflated to its unextended or working profile and then therebeyond to a limited and/or controlled extent by the application of greater pressure. Each balloon 33 and 34 includes a balloon portion 35, 36, respectively, and leg portions 37, 38, respectively. The leg portions 37, 38 are the portions of the balloon that are secured to the tube 22 of the catheter 21.

In an exemplary application, tubing length 32 is extruded so that it exhibits a diameter that is roughly one-quarter of the diameter intended for the balloon. The extruded tubing length 32 also has a nominal wall thickness that is on the order of six to twelve or so times the desired wall thickness of the balloon 33, 34.

FIG. 2b illustrates tubing length 32a, which is tubing length 32, after it has been axially oriented or elongated to approximately three times its original length. This elongation or drawing procedure is carried out at approximately room temperature, and same proceeds typically until it has been stretched to the point that it exhibits a noticeable resistance to further stretching. Typically, the pull force is greater than the yield point of the particular tubing length 32, but less than the ultimate tensile strength, lengthwise, of the selected material. Generally speaking, this axial elongation procedure is carried out until the wall thickness of the tubing length 32a is roughly one-half of the wall thickness of the tubing length 32 and/or until the diameter of the tubing length 32a is roughly one-half to forty percent of the outer diameter of the tubing length 32. The actual stretched length can typically be about two times to about four times or more of the original tubing length 32. Actual stretching of the tubing 32 can be performed by simply axially stretching length 32 or by pulling or drawing length 32 through a sizing die.

FIG. 2c illustrates a step that is carried out after the longitudinal orientation procedure of FIG. 2b has been completed. This is a biaxial orientation step by which a portion of the tubing length 32a expands primarily radially and thereby delineates the balloon portion 35 from the leg portions 37. This biaxial orientation is carried out by pressure exerted on the inside wall of the tubing length 32a by a pressurized fluid. Typically, the balloon portion 35 will have an outer diameter that is on the order of roughly six times the outer diameter of the tubing length 32a. The pressurized fluid may include gasses such as compound air, nitrogen or argon. Liquids such as water or alcohol could also be used if they do not pose a problem of leaving residual fluid in the balloon. Generally speaking, the larger the balloon, the faster will be the inflation fluid flow rate. Examples of cardiac balloons generally ranked in typical order of increasing size are those designed for use in coronary arteries, those designed for use in peripheral arteries, and valvuloplasty balloons for use in cardiac valves. Other balloons include uroplasty balloons for dilating the prostatic urethra.

The procedure illustrated in FIG. 2c can be facilitated by controlling the location at which the biaxial orientation will occur. An advantageous manner of effecting this result is to carry out a local application of heat to the balloon portion 35 during radial expansion while avoiding such heat application at the leg portions 37. Elevating the temperature in such a localized area will lower the yield point of the nylon, polyamide or the like at that location and thereby facilitate the biaxial orientation of this selected area. As an example, a temperature for conducting this step typically can be between about 35° C. and perhaps as high as 90° C., the optimum temperature depending somewhat upon the particular material that is utilized.

Means are provided for controlling the expansion or axial orientation of the tubing length 32a and its formation into the balloon portion 35 and the legs 37. This can be accomplished by controlling and monitoring conditions and/or expansion positions within a molding apparatus. An exemplary means in this regard is included in the molding apparatus described herein. Otherwise, this function can be accomplished by closely controlling the rate of fluid passage and by monitoring the pressure thereof. For example, for a valvuloplasty balloon, the following approach can be taken. One end of the longitudinally oriented tube having a diameter of approximately 0.140 inch and a wall thickness of approximately 0.006 inch is sealed, and a liquid such as water is pumped into the tube at a rate of approximately 2 ml per minute. For tubing of this size and at a flow rate of this magnitude, balloon inflation begins at about 300 psi gauge and drops to around 150 psi gauge. Expansion continues in this manner until the wall of a mold bearing the desired shape of the balloon is encountered, which is observable by a significant pressure increase. Pumping continues until a pressure of about 180 to 200 psi is reached. This pressure condition can be held or maintained, if desired.

A satisfactory balloon can be prepared by proceeding with the method through and including the step illustrated in FIG. 2c, followed by dimensional stabilization, heat setting or thermoforming, the balloon to near its biaxially oriented profile and size by maintaining its elevated temperature until the selected material is thermally set. Tailorability that is achieved according to this invention is a function of the particular heat setting conditions. The setting temperature can vary with the type of material used, the wall thickness, and the treatment time. A typical setting temperature is between about 100° C. and about 160° C. for a nylon material, and a typical time is from about 1 minute to about 4 minutes.

Such balloons 33 may include expansion knurls 39 that tend to appear in the areas generally extending between the legs 37 and the working surface of the balloon portion 35. These expansion knurls, which may be described as nodules, ridges, ribs, beads or the like, are believed to result from disproportionate expansion or orientation of the material such as nylon in this area. When it is desired to minimize the existence of these expansion knurls 39 on the balloon, secondary longitudinal orientation with radial shrinkage followed by secondary radial expansion can proceed with a balloon that is not thermally set, such being illustrated in FIG. 2d and FIG. 2e.

Regarding FIG. 2d, the balloon 33 of FIG. 2c, which is not thermally set, is again longitudinally oriented by applying an axially directed force that is typically greater than the yield point but less than the ultimate tensile strength of the balloon 33. If desired, the magnitude of this axial force can be substantially the same as the magnitude of the axial force applied in the procedure illustrated in FIG. 2b. Further biaxial orientation is then conducted by, for example, introducing a pressurized fluid into the balloon lumen in order to prepare the balloon 34 shown in FIG. 2e. It is often desirable to conduct this procedure within a mold cavity in order to thereby effect a careful shaping of the balloon portion 36, the leg portions 38, and the tapered connection surfaces therebetween, generally as desired. The resulting modified balloon 34 typically will not include any significant expansion knurls 39, and it will exhibit a uniformly oriented transition between the balloon portion 36 and the leg portions 38. This additional longitudinal expansion or stretching substantially eliminates areas of non-oriented material.

Whether the procedure is utilized that forms the balloon 33 or if the procedure is continued such that the balloon 34 is formed, the thus formed balloon 33, 34 is preferably then subjected to a heat setting step at which the still pressurized balloon 33, 34 is heated to set the expanded dimensions thereof. Setting will typically be accomplished at a temperature of 85° C. or greater, typically up to about the melting point of the balloon material, depending somewhat upon the actual material and the size and thickness of the balloon. For example, a typical heat setting temperature for Nylon 12 is 1 minute at 120° C. With this heat treatment, the balloon will retain this form and most of its expanded size, typically about 95% of more of it, upon being cooled. Preferably, the balloon remains pressurized until it is generally cooled. If this heat setting procedure is not utilized, the balloon will promptly shrink back to approximately 40% to 50% of the diameter to which it had been blown or biaxially oriented in the mold.

With more particular reference to this heat setting procedure, an important component in this regard is the use of a thermoformable material. A material is thermoformed if it can be formed to another shape. Nylon is a thermoforming plastic. It can be heated to a temperature below its melting point and deformed or formed to take on another shape and/or size. When cooled, thermoforming materials retain that new shape and/or size. This procedure is substantially repeatable. On the other hand, a thermosetting material, such as a natural latex rubber, a crosslinked polyethylene or a silicone rubber, once "set" is crosslinked into that size and/or shape and cannot be heat deformed. Also, biaxially oriented polyethylene terephthalate tends to crystallize and lose the thermoforming ability that is typical of polyethylene terephthalate which is not biaxially oriented. When a biaxially oriented nylon balloon is heated for a prolonged period of time at temperatures greater than a predetermined elevated temperature, for example about 80° C., and then cooled, it becomes thermoformed to the balloon geometry. If the balloon were to be reheated to this temperature or above, it could be formed into a balloon having a different geometry.

FIG. 3 illustrates a molding apparatus that is suitable for fabricating medical balloons as discussed herein. The apparatus transforms a parison 41 into balloons for medical devices and the like. The apparatus achieves longitudinal stretching, biaxial orientation, heating and cooling, and it includes means for monitoring radial expansion or biaxial orientation, all of which can be conveniently controlled by suitable means such as hard circuitry, a microprocessor, or other computerized controlling arrangements. These various parameters that are controlled can thus be precisely set and easily modified in order to present the optimum conditions for fabricating a particular parison into a balloon having a specified sizing and the properties desired. Specific parameter values are presented herein which are typically suitable for balloon materials such as nylons, and it will be understood that these parameter values can be modified as needed for the specific material being shaped into the balloon.

The apparatus that is illustrated also has the ability to generally simultaneously perform different steps on multiple balloon portions of the parison 41 as it passes through the apparatus. This can be especially useful because of variations in wall thickness and other attributes of each batch of tubing that is used as the parison 41.

The apparatus includes a series of components which are suitably mounted with respect to each other, such as along slide rails 42. From time to time, movement of some of the components along the rails or the like is carried out by suitable means, such as piston assemblies (not shown) in accordance with generally known principles and structures.

A pressurized fluid supply 43 is provided to direct pressurized fluid into an end portion of the parison 41, typically in conjunction with one or more regulators 44 in accordance with well-known principles. One or more valves 45 also assist in controlling the flow rate and volume of pressurized fluid within the parison 41. Gripper assemblies 46 and 47 are provided for engaging different locations of the parison 41. An intermediate gripper assembly 48 is preferably also provided. One or more chiller chambers 51, 52, 53, 54 are also preferably provided. These are particularly useful as means for thermally isolating assemblies of the apparatus from each other. Also included are a free-blow biaxial orientation chamber or mold 55 and a molding chamber 56.

Preferably, means are provided by which the temperature of these various chambers is controlled and/or varied, for example between about 0° C. and about 150° C. or more. The illustrated assembly in this regard includes a jacket for confining a thermal fluid that is pumped thereinto and out thereof by suitable fluid inlets 57 and fluid outlets 58. O-rings 59 or the like are provided in order to contain the thermal fluid within each fluid jacket 61, 62, 63, 64, 65, 66.

In using the illustrated apparatus, the parison 41 is initially fed or threaded through the entire apparatus, typically between gripper assembly 46 and gripper assembly 47. Gripping pads 68 of the gripper assembly 47 move inwardly and engage the downstream end portion of the parison 41 to the extent that it pinches off this portion of the parison 41, preferably also heat sealing the parison at this time. Generally simultaneously, gripping pads 67 of the gripper assembly 46 engage the parison 41 at the illustrated upstream location of the apparatus to such an extent that the gripping pads 67 will prevent movement of the parison 41 with respect to the gripping pads 67, but still permit the flow of pressurized fluid thereacross when desired. Gripper assembly 47 then moves in a downstream direction (to the right as illustrated in FIG. 3) until the length of the parison that is secured between gripper assemblies 46 and 47 is stretched or longitudinally oriented to in excess of twice its length up to as great as about four times its length or more, a typical stretching being approximately three times this unstretched length.

Next, the free-blow biaxial orientation chamber 55 is heated by passing heated thermal fluid into the fluid jacket 62. The chiller chambers 51, 52, or other suitable means, provide a thermal variant such that the heat from the fluid jacket 62 is imparted only to that length of the parison that is substantially within the free-blow biaxial orientation chamber 55. The temperature of this particular portion of the parison 41 will be heated to a temperature of roughly between about 70° C. and 120° C. or more, depending upon the particular parison 41 and the balloon properties desired. At this time, pressurized fluid within the parison 41 that originates from the supply 43 passes through the parison length at the gripper assembly 46 and into the parison length at the free-blow chamber 55. If desired, the gripper assembly 48 can be utilized in order to confine this particular pressure application to the section of the parison 41 that is upstream thereof.

A primary objective of the free-blow biaxial orientation chamber 55 is to radially expand that portion of the parison 41 into a balloon 33 as generally illustrated in FIG. 2c. It is often desired to precisely control the amount of biaxial orientation, and means in this regard are provided. The means illustrated in FIG. 3 includes a slidable insert or ring 69. When this insert 69 is engaged by the expanding balloon 33, it moves against an air or metallic spring (not shown) in a direction to the left as illustrated in FIG. 3 until it trips a suitable switch or the like (not shown), which signals that the desired degree of biaxial orientation has been achieved. At this time, steps are taken to interrupt the biaxial orientation. This typically includes cooling by exchanging the heated thermal fluid within the fluid jacket 62 for thermal fluid having a colder temperature, typically on the order of about 10° C. or somewhat above or below depending upon the particular parison 41 and the particular properties desired.

The pressure imparted to balloon portion 33 is then depleted by, for example, permitting exhaustion thereof through the valve 45 after the balloon has been cooled. If utilized, the gripper assembly 48 is released, and the balloon portion 43 is moved from the free-blow biaxial orientation chamber 55 into the molding chamber 56 by movement of the downstream end portion of the parison by the gripper assembly 47. This typically simultaneously accomplishes the longitudinal orientation stage depicted in FIG. 2d. Once this positioning takes place, the pressurized fluid is pumped into that portion of the parison that is within the molding chamber 56, and thermal fluid is passed into the fluid jacket 65 in order to heat this portion of the parison to an elevated temperature, again between about 70° C. and up to just below the melting point, for example 150° C. or more, depending upon the particular parison and the properties desired of the balloon.

Generally speaking, it is usually advantageous that the temperature in the molding chamber 56 be higher than that applied in the free-blow chamber 55, while at the same time imparting a pressure to the inside walls of the parison within the molding chamber 56 that is equal to or lower than the pressure applied in the free-blow chamber 55. For example, when a nylon is the material, the temperature in the free-blow chamber 55 can be slightly above ambient, preferably in a range of between about 30° C. and 60° C., while the temperature in the molding chamber 56 can be at the high end of this range or even well above, as needed. Exemplary pressures would include on the order of ten atmospheres in the molding chamber 56 and twice that pressure or greater in the free-blow biaxial orientation chamber 55. The exact pressure is determined by the material and by the wall thickness and hoop stress of the balloon to be molded.

With heat thus imparted to the modified biaxially oriented balloon 34 within the molding chamber 56, the balloon 34 is thereby thermoformed, with heat setting in this regard involving raising the temperature of the thermoplastic while it is under inflated stress. Thereafter, the heated fluid within the fluid jacket 65 is exchanged for cooling fluid in order to substantially maintain the size and shape of the balloon 34 formed within the molding chamber 56. After the pressure has been relieved, the balloon is removed from the apparatus. Subsequently, the thus modified parison is severed generally along lines A and B as illustrated in FIG. 2e in order to thereby form the balloon 26 for inclusion within a medical device such as the catheter 21.

It will be appreciated that the parison will include balloons in various stages of their formation as the parison passes through the apparatus. Preferably, this is accomplished in a somewhat reverse manner, as follows. After initial stretching and formation of a balloon 33 within the free-blow chamber 55, the apparatus is utilized so that the portion of the parison within the molding chamber 56 is radially expanded before that within the free-blow chamber 55, which generally occurs as follows. Molding chamber 56 is heated as described herein and pressurized to form the balloon 34. Thereafter, the gripper assembly 48 closes off the parison between the chambers 55 and 56. The free-blow chamber 55 is then heated, and the biaxial orientation is carried out as described herein in order to form the balloon 33. Balloon 33 is then moved into the molding chamber 56, and the process is essentially repeated.

It should be appreciated that the balloon can be made entirely in the mold section 56 without free blowing in compartment 55. However, balloons made in this manner may demonstrate knurling.

Regarding the fluids suitable for use in the apparatus, it is typically advantageous to have the pressure source 43 provide a fluid that does not require excessive treatment to remove same from the internal surfaces of the finished medical device balloon 26. To be taken into consideration in this regard are moisture content of fluids and ease and safety of disposal of the fluid. A particularly suitable fluid is pressurized nitrogen gas. With respect to the fluid for use within the various fluid jackets 61 through 66, it is typically best to utilize a fluid that is in its liquid state throughout whatever processing temperatures might be needed for the apparatus. Preferably the fluid is one that will likewise maintain a generally consistent viscosity throughout the processing range, for example, avoiding the onset of solidification or crystal formation or the like that would modify the properties of the thermal fluid at lower processing temperatures.

With respect to the materials out of which the balloon and parison are made, they are typically nylons or polyamides. Preferably, these materials have an amorphous nature while still possessing enough crystallinity to be biaxially oriented under the conditions provided according to this invention. The materials should also have substantial tensile strength, be resistant to pin-holing even after folding and unfolding, and be generally scratch resistant. The material should have an intrinsic viscosity that enables blowing at elevated temperatures. A typical intrinsic viscosity range that is preferred for the nylon or polyamide materials according to this invention is between about 0.8 and about 1.5, with about 1.3 being especially preferred. It is also desired that the material have a reasonably good moisture resistance. Materials of the Nylon 12 type have been found to possess these advantageous properties. Other exemplary nylons include Nylon 11, Nylon 9, Nylon 69 and Nylon 66.

With more particular reference to the intrinsic viscosity of nylon or polyamide materials, it is believed that such materials are able to generally maintain their intrinsic viscosities during extrusion and through to final balloon fabrication. It is further understood that other materials such as polyethylene terephthalate which have been used to fabricate balloons for medical devices typically do not exhibit this maintenance of intrinsic viscosity, but the intrinsic viscosity of the pellet material drops substantially during extrusion, with the result that a biaxially oriented polyethylene terephthalate balloon is understood to have an intrinsic viscosity which is lower than that of the polyethylene terephthalate pellets from which it originated. It is further believed that a higher balloon intrinsic viscosity reduces the likelihood that pin-holing will develop in the finally fabricated balloon.

With further reference to the nylon or polyamide materials which may be used according to this invention, they are bondable to the catheter 21 by epoxy adhesives, urethane adhesives, cyanoacrylates, and other adhesives suitable for bonding nylon or the like, as well as by hot melt bonding, ultrasonic welding, heat fusion and the like. Furthermore, these balloons may be attached to the catheter by mechanical means such as swage locks, crimp fittings, threads and the like. Nylon or polyamide materials can also be provided in the form in which they are reinforced with linear materials such as Kevlar and ultra high tensile strength polyethylenes. The polymer materials used can also be coated with pharmaceutical materials such as heparin and the like, non-thrombogenic lubricants such as polyvinyl pyrrolidone and the like. Additionally, the polymer materials can be filled with radiopaque media such as barium sulfate, bismuth subcarbonate, iodine containing molecules, tungsten, or other fillers such as plasticizers, extrusion lubricants, pigments, antioxidants and the like.

Nylons or polyamides as used according to the present invention are flexible enough to tolerate a greater wall thickness, even in the leg areas, while still providing a structure that is foldable onto itself for insertion into a body cavity or guiding catheter. These nylons or polyamides, when biaxially oriented and formed into balloons as discussed herein, have a calculated tensile strength of between about 15,000 and about 35,000 psi and above, preferably between about 20,000 and about 32,000 psi.

The materials according to the present invention form medical device balloons that exhibit the ability to be expanded first to a non-stretched or non-distended condition, or working size, upon the application of a given pressure. They also have the ability to be inflated further so as to be stretched therebeyond in a controlled and limited manner. The degree of such stretching or expansion can, within limits, be tailored as needed. In other words, the balloons according to the present invention allow for some growth at a pressure higher than that needed to merely fill the balloon, but this additional growth or expansion is not so substantial that there is an overinflation danger.

Materials according to this invention should be able to be tailored during balloon formation to possess the ability to be stretched a generally predetermined percentage beyond its non-distended or working diameter, the amount of this percentage depending upon conditions under which the parison was processed into the balloon. A suitable material according to the present invention can be tailored to cover values within a span of at least 10 percentage points of radial expansion. Certain materials including some nylons can exhibit a tailorability range of 25 or 30 percentage points or more and can, for example, exhibit a radial expansion of 10 percent or below and as high as about 30 percent or above.

In order to illustrate this situation, tests were run on angioplasty balloons of different materials, namely polyvinyl chloride, cross-linked polyethylene, polyethylene terephthalate and nylon. These data are reported graphically in FIG. 4. Wall thicknesses varied depending upon the properties of the material in order to provide a viable balloon. The polyethylene terephthalate balloon (B) had a wall thickness of 0.010 mm. The polyvinyl chloride balloon (C) had a wall thickness of 0.064 mm, and the polyethylene balloon (D) had a wall thickness of 0.058 mm. (Data for balloons C and D are as reported in "Effects of Inflation Pressure on Coronary Angioplasty Balloons," *The American Journal of Cardiology*, Jan. 1, 1986, these tests being run under ambient conditions, while the remaining balloons in FIG. 4 were tested at 37° C.) One of the nylon balloons (A) had a wall thickness of 0.013 mm and a hoop expansion ratio of 5.2. Another of the nylon balloons (E) had a wall thickness of 0.008 mm and a hoop expansion ratio of 4.3. Tailorability of balloons according to this invention is a function of hoop expansion ratio, which is defined as mean balloon diameter divided by mean as-extruded tubing or parison diameter. Typically, such hoop expansion ratios range between about 3 and about 6.

FIG. 4 plots the relative pressure of the fluid imparted to the various angiographic catheters against the percentage increase in size (such as diameter or radius) of the balloon beyond its working size, designated as "0." It will be noted that the more compliant materials, such as polyvinyl chloride, gradually grow with increased pressure and permit some limited additional pressure increase after the working size has been achieved and before further expansion ceases prior to reaching the burst limit of the balloon. It will be appreciated that, with materials such as these, a smaller increase (when compared with materials of plots A and B) in relative pressure significantly increases the balloon size. Materials such as polyethylene terephthalate (PET) inflate to their working size, but not therebeyond to an extent as great as others of the plotted curves.

The nylon or polyamide material illustrated by curve E exhibits a relatively long and flat curve in FIG. 4, which indicates that it will continue to expand moderately upon the application of relatively small additional increments of inflation pressure. Once the unstretched or non-distended profile or working size is reached, this tailored nylon balloon possesses adequate stretchability or compliance to the extent that it can ramp up to another inflated profile. While the polyethylene balloon of curve D initially distends to about the same extent as does the nylon curve E balloon, this nylon balloon can tolerate greater inflation pressures without bursting than can the curve D polyethylene balloon or the curve C polyvinyl chloride balloon. This observation is especially significant when it is appreciated that the curve E nylon balloon had a substantially thinner wall diameter. Based upon data such as that illustrated in FIG. 4, it is possible to predict the compliant expansion associated with added inflation pressure. A balloon in accordance with the present invention can exhibit this growth property so that it will radially expand from a low of about 5 percent beyond the working size to a high of about 35 percent or more of the working size.

As previously observed herein, balloon expansion tailorability is a function of heat setting conditions and of hoop expansion ratio for balloon materials according to the present invention. For such materials, increasing the heat set temperature increases the size of the finished balloon at a given inflation pressure and decreases the shrinkage which typically occurs after sterilization such as a standard ethylene oxide treatment. Also, the amount of hoop expansion imparted to the parison during processing has a significant effect on the amount of distention which the finished balloon will exhibit.

FIGS. 5 and 6 illustrate the effect of varying heat setting conditions on the distensibility of the finished balloon. This heat setting is achieved when the biaxially oriented balloon is subjected to a temperature greater than the glass transition temperature of the balloon material and is allowed to cool to below the glass transition temperature. For a material such as a nylon or a polyamide, temperatures between about 90° C. and about 180° C. have a pronounced heat setting capability. The glass transition temperatures may be less than this heat setting temperature and may include temperatures in the range of 20° C. to about 40° C., and the balloon will exhibit good flexibility at body temperature which can, for example, facilitate balloon insertion and maneuverability during use.

FIG. 5 gives four distention plots, tested at 37° C. for nylon balloons that are substantially identical except they were subjected to different heat set temperatures. In each case, the balloon was subjected to a 2 minute heat/cool cycle, with cooling being to room temperature. Each balloon was subsequently subjected to ethylene oxide sterilization. Curve F was subjected to a heat set temperature of 120° C., curve G was at 130° C., curve H was at 140° C., and curve I was at 150° C. It will be noted that the curves illustrate different distention properties and the type of tailoring thus achieved. FIG. 6 provides a similar illustration and further shows an effect of the ethylene oxide sterilization. While curves J and K both are for balloons which were heat set at 100° C., the curve J balloon was sterilized while the curve K balloon was not. Likewise, the balloons of curves L and M both were heat set at 140° C., curve L illustrating a sterilized situation, and curve M a non-sterilized situation.

The relationship between balloon tailorability and hoop expansion ratio is illustrated in FIG. 7. Three non-sterilized nylon balloons having different hoop expansion ratios were tested at 37° C., the expansion being to burst. A relatively high hoop expansion ratio of 4.9 (curve N) gave a balloon distention (safely short of burst) of about 7 percent. A 3.7 hoop expansion ratio (curve O) gave a balloon distention of about 23 percent, while a 3.3 hoop expansion ratio (curve P) gave a balloon distention of about 36 percent.

Furthermore, nylon or polyamide balloons according to the present invention provide controlled expansion properties and tolerate given pressures without bursting without requiring wall thicknesses as great as those needed for other materials such as polyvinyl chloride or polyethylene. This thin wall thickness of these nylon balloons permits the balloon to enter smaller vessels, lesions and/or catheters. Suitable balloons according to this invention can have shell or wall thicknesses as low as about 0.0002 inch and as high as 0.002 inch. An exemplary preferred shell thickness range is between about 0.0004 and about 0.001 inch, or between about 0.0005 and about 0.0008 inch.

A material such as nylon is softer and more flexible at body temperature, the temperature at which it is used, than other balloon materials such as polyethylene terephthalate which have a glass transition temperature far in excess of body temperature. For at least some nylons, the glass transition temperature approximates body temperature, and nylon balloons generally exhibit amorphous properties that enhance flexibility and softness even after proceeding with the type of processing described herein, including thermoforming and the like. Nylon balloons thus can be at a glass transition state while they are within the body, which is not the case for numerous other materials that can be used as medical balloons.

Balloons made of nylons exhibit a property such that, when they burst, the diameter of the balloon will decrease, thereby facilitating removal from the body. It is believed this decrease may be caused by a relaxing of the material which noticeably reduces the size of the balloon. Other materials such as polyethylene terephthalate are not known to exhibit this advantageous property. A disadvantageous property that can be characteristic of polyethylene terephthalate medical balloons is the development of extensive material wrinkling upon sterilization, which wrinkles persist, even at body temperature, until very high inflation pressures are applied, on the order of 200 psi. When a nylon or polyamide balloon is sterilized, few if any material wrinkles develop, and these substantially disappear at relatively low inflation pressures, on the order of 8 psi.

Nylon materials have been observed to exhibit desirable stability during processing to the extent that they do not absorb excessive moisture from the environment if the parison is allowed to stand uncovered for reasonable time periods. Materials such as polyethylene terephthalate are degraded by environment moisture if the parison is not stored in protective bags or the like prior to biaxial orientation.

It will be understood that the embodiments of the present invention which have been described are illustrative of some of the applications of the principles of the present invention. Numerous modifications may be made by those skilled in the art without departing from the true spirit and scope of the invention.

We claim:

1. A process for tailoring expansion properties of a balloon for a medical device, the process comprising the steps of:

longitudinally stretching a length of biaxially orientable tubing having an initial diameter and made of material capable of being tailored by the steps hereof to provide drawn tubing;

radially expanding the thus drawn tubing to form a balloon member, said balloon member having a non-distended working diameter and having a hoop expansion ratio, which hoop expansion ratio is an approximate ratio of said non-distended working diameter to said initial diameter of the tubing; and said radially expanding step including selecting said hoop expansion ratio such that the balloon member exhibits a tailored maximum inflated diameter to which the balloon stretches without bursting during dilatation, said hoop expansion ratio being selected in accordance with the fact that said maximum inflated diameter increases as said hoop expansion ratio decreases.

2. A process according to claim 1, wherein said hoop expansion ratio is between about 3 and about 6.

3. The process according to claim 1, further including heat setting said balloon member by raising the temperature of the balloon member to a heat setting temperature above the glass transition temperature of the biaxially orientable tubing material, followed by cooling the balloon member to a temperature below the glass transition temperature, said heat setting temperature being selected in accordance with the fact that said maximum inflated diameter increases as said heat setting temperature increases.

4. The process according to claim 3, wherein said heat setting temperature is between about 90° C. and about 180° C.

5. The process according to claim 3, wherein said glass transition temperature approximates human body temperature.

6. The process accordance to claim 3, wherein said temperature below the glass transition temperature approximates room temperature.

7. The process according to claim 3, wherein said heat setting step maintains said heat setting temperature for between about 1 minute and about 4 minutes.

* * * * *